United States Patent [19]
Ting et al.

[11] Patent Number: 6,022,741
[45] Date of Patent: Feb. 8, 2000

[54] REGULATORY GENETIC DNA THAT REGULATES THE CLASS II TRANSACTIVATOR (CIITA)

[75] Inventors: Jenny Pan-Yun Ting; Janet Piskurich, both of Chapel Hill, N.C.

[73] Assignee: University of North Carolina at Chapel Hill, Chapel Hill, N.C.

[21] Appl. No.: 08/816,617

[22] Filed: Mar. 13, 1997

[51] Int. Cl.⁷ .............................. C12N 5/08; C12N 1/00; C12N 5/10; C12N 15/11

[52] U.S. Cl. ..................... 435/366; 435/243; 435/320.1; 435/325; 435/410; 536/23.1; 536/24.1

[58] Field of Search ................................ 536/24.1, 23.1; 435/320.1, 325, 410, 366, 243

[56] References Cited

PUBLICATIONS

Chin et al.; "Molecular Analysis of G1B and G3A IFNγ Mutants Reveals that Defects in CIITA or RFX Result in Defective Class II MHC and li Gene Induction"; *Immunity*, 1:687–697 (1994).

Devajyothi et al.; "Inhibition of Interferon–γ–induced Major Histocompatibility Complex Class II Gene Transcription by Interferon–β and Type β1 Transforming Growth Factor in Human Astrocytoma Cells"; *J. of Biol. Chem.*, 268:18794–18800 (1993).

Improta et al.; "Transcription factor ISGF–3 formation requires phosphorylated Stat91 protein, but Stat113 protein is phosphorylated independently of Stat 91 protein"; *Proc. Natl. Acad. Sci. USA*, 91:4776–4780 (1994).

Panek and Benveniste; "Class II MHC Gene Expression in Microglia–Regulation by the Cytokines IFN–γ, TNF–α, and TGF–β"; *J. of Immunology*, pp. 2846–2854; © 1995 by The Amer. Assoc. of Immunologists 0022–1767/95.

Reimold et al.; "Transforming Growth Factor β₁ Repression of the HLA–DRα Gene Is Mediated by Conserved Proximal Promoter Elements"; *J. of Immunology*, 151(8):4173–4182 (1993).

Riley et al.; "Activation of Class II MHC Genes Requires Both the X Box Region and the Class II Transactivator (CIITA)"; *Immunity*, 2:533–543 (1995).

Zhou and Glimcher; "Human MHC Class II Gene Transcription Directed by the Carboxyl Terminus of CIITA, One of the Defective Genes in Type II MHC Combined Immune Deficiency"; *Immunity*, 2:545–553 (1995).

A. Lennon et al.; "Isolation of a B–cell–specific promoter for the human class II transactivator"; *Immunogenetics*, 45:266–273 (1997).

Genebank, Accession No. U67329, published Mar. 29, 1997; A. Lennon et al.; "Isolation of a B–cell–specific promoter for the human class II transactivator", *Immunogenetics*, 45:266–273 (1997).

V. Steimle et al.; Complementation Cloning of an MHC Class II Transactivator Mutated in Hereditary MHC Class II Deficiency (or Bare Lymphocyte Syndrome), *Cell*, 75:135–146 (1993).

*Primary Examiner*—Terry McKelvey
*Attorney, Agent, or Firm*—Myers Bigel Sibley & Sajovec, P.A.

[57] ABSTRACT

Novel DNAs that regulate expression of the Class II Transactivator (CIITA) gene are disclosed. Recombinant DNA comprising CIITA regulatory elements operably associated with a heterologous DNA are also disclosed. Additionally, assay systems for identifying compounds that regulate expression of the class II major histocompatibility (MHC) antigens are also disclosed.

40 Claims, 6 Drawing Sheets

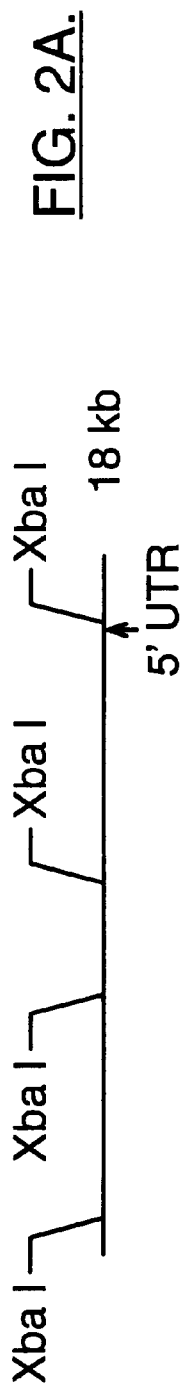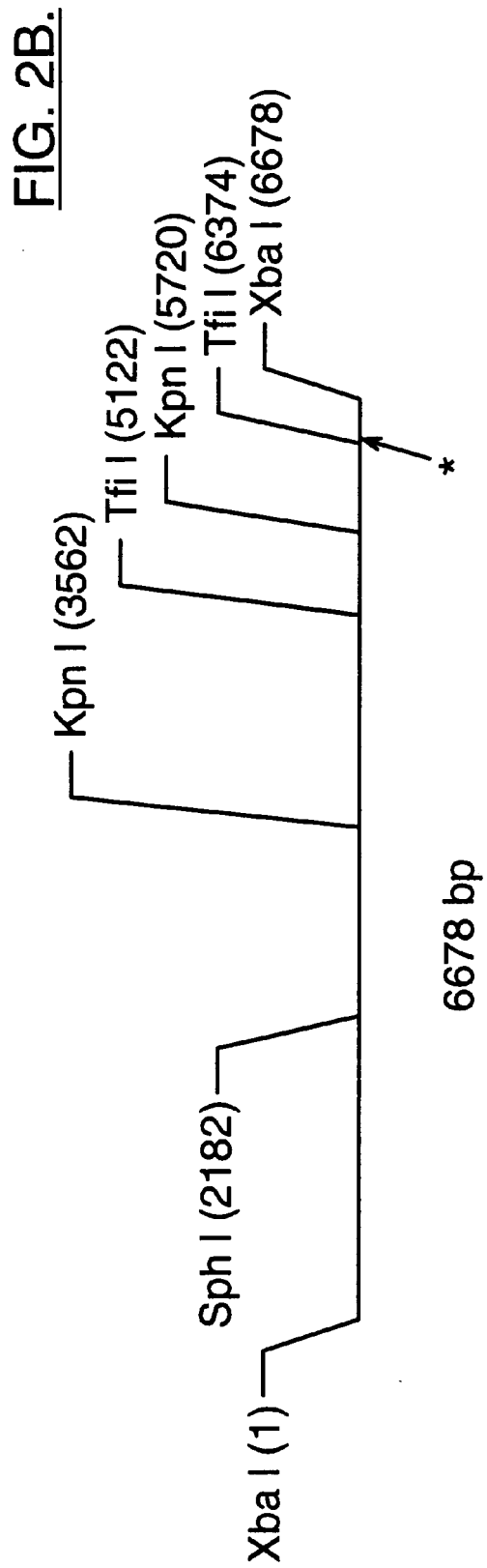

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 6678 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:1:

```
TCTAGACACC TACCCCATGC AAAATGCAGT GCTGAGTGCT TGGGTACTGT GCATATTTGA      60

GAAACAAATC AATGTGGCCC CTGCCCTCGA GTTGAACTGG CACATGGGCC ATGTCCTCAG     120

ACAGCCTGAG TGCCTGTCCT GCCTTCCCAA TTCCAAGAGG TATGACTTTG AGCACTTCCC     180

GGGCGCCCCG CCTCAGTTTC CCCATCTATA AAGTGGAGAT GATAATAGCA TTCAGAGTCA     240

CTGATCTAAG GGCTCAGGGA CACCATTCAG TGTAAGCCCC ATACACTCCC TGCAAGAGGA     300

AGCTGGTTCT GACTCAGCCT TGAGGCTGGC GTCTGAGGCA ACCACAAGCC CAACGTGCAT     360

GGTGGAAAGA TGACTGTAAG TGGGGGCAAC CTCAGCTGGC CTTGGGTTTG ACCATGGAAT     420

GCGAGGCACA AAGGGGCCCA TTTTGCATAC TTTCTCAGAG GCTGTAGGGC ACCCCTGCCA     480

GGGTCTTACA TTTTATTGAT TCCTCTGACT CTACTTTGTT GGTTGTTTTT GTTGTTCTGA     540

TTTCATTGCG TGACATTTTT GCCCATGAGG TCTCAGTTCT AGGAATGACA GAACAAAGGC     600

TCCCTCTGGG AAGTCGCCTG ATTTATTGGA AAGGGAGGAA CACCCCACCC TTAGGGATCG     660

CTAAGCTCCC TTCCTCCAGC TTCCTTCCCC ATCTGGCCCT TAGGATGTGA GAAACCAGAG     720

CTGTGACACA CCAGAGAGGA GAGAGGCTGT GCCCTCTCAC CTTCTGGGCT TCCTTTCCTG     780

AGAACCAGCC CCTGTTCTGA TTTTGGGAGT CTCCTTTGCC TCAGGGAGGG GGATGTGTTG     840

GCGAGGAAGA CTCGTGCCTT TCATCTTGGA CTGCTTCTCT GGCCCTCTAC CCCAGGAACC     900

ACAGAAGGAG ACACACCTGT ACCCGGAAGC TGGCATTTCC CCATGGGTTT TCCCAGGCCA     960

GCCTGTTCCA AACACAGCTT GCCCCAAGC CTGGCACTTC TCCAACCAGT CACGGTTTCT    1020

GTTCTCTGTT GCTATGACCT TGAGCAGTTC ACCTGCGTTC CTTACTGTCT ACTTTCCCAT    1080

CCACCTACCT GCCTGCCCTC CAACTTTCCT GATCTGTGTA CCTACCTTCC TATATCTACT    1140

TCTTTTTATT ATTATTATCA TTATTCTCAC CCTGTCTTTT TTTTAATTTT TTTTGGGTGG    1200

GGGGGACACA GTCTTGCTTT GTAGCCCAGG CTGGAATGCA GTGGCGTGAT CTCAGCTCAT    1260

TATAACCTCT GCCTCCCAGA TTCAAGCAAT TCTCCTGCCT CAGCCTCCCG AGTAGCTAGG    1320
```

```
ATTACAGGCG CCTGCCACCA TGCCGAGCTA ATTTTTATAT TTTTAGTAGA GACAGGGTTT    1380

CATCATGTTG GCCAGGCTGG TCTCAAACTC CTGACCTCAA GCAATCCACC CATCTCAGCT    1440

TCCCAAAATG CTGGGATTAT AGGCGTGAGC CACTGTGCCC AGCCTCTCGC CCTGTCTTAT    1500

GGTGGTAATC TACTTCTCAA TTTATCTATT TATATCTACT GTCTACATAC TTATACACTT    1560

ATTTACTCAT GTCTACTTAT CAGTTAATCC ATTTCTCTAC CTACCTAATC ACCCATATAT    1620

TTCCCATGTA TTTACATGTC AAAGTATTTC CCTGCATTCC TACCAGCTAA GCCCCCTTTA    1680

CAACAATCCA TCAGCAGGTC CAGGTTCTCA TACACCCTCC CATGTCCCTC CCTAATTTGG    1740

ATACATAGCA GTTGTATTCT ACTCACCTAT CTCCCTATTC ACCGATCTCT TTCTCTCCCT    1800

TTCTTGCCTC CTTTCTTTCC TTCTCCTGAA TCATTTATTT AGCACCTGCT AGAAATTATG    1860

GTGGACTCCC CATCCAGTGC TCTTTCACCA AAAAGCATGA GATGAAGAAG GACTTTTAAC    1920

CTAGTAGGGG AGGAATCTTC ATCCATTTGG AACTGGAGGC TGCCTTGATC ATTCAAATCT    1980

AAAACTCCAT TCATTCCTTC AAATGGTCTT AGAATAGTGT ATCTTCTATT TTATTATTTT    2040

ATTTTATTTT TTGAGACAGG GTCTTGCTCT GTCGCCAAGG CTGGAGCACA GTGGCGCAAT    2100

CACAGCTCAC TACAGCCTCA ATCTCCTGGG CTCAAGACAT CCTCCCATCT CAGCCTCCCA    2160

AGTAGCTGGG ACTACAGGCA TGCACCACTA TGCCCGGCTA ATTTTTTTAT TTGTGGTAGA    2220

GATGAGGTCT CGCTATGTTT CCCACGGCTG GTCTCAAACT TCTGGGCTCA AGCGACATAC    2280

CTGCCTTAGC CTCCCAAAGT GCAGTGTGCC ACTGCACCTC GCCTGATAAT GTGTCTTTCA    2340

AATGCTCAGT CTTGTGTAGG TATTGGGGTA AGTGCAGAAA ATTAAAGACC TGATCCTAGA    2400

CATTAACAGA TGTATGATCT AATCAGAGGT AGCAGAGATG ATGCTTATGA ACTTGAAAGT    2460

TAAAGTTGTA TTGCCAAATA ATGTTGCAGC AAGTTTTGTA AAACACAGCA AAGCAAGAAA    2520

ATTATAGTTA GCTGGAAGCG CGATGAAGGT GGGAACTCGA GCTTTGCAGG ATGGCTAAAA    2580

TATAGACCAA AAGGGAGAAG GCAGGAGAGC AGCACCGGGA GGGAGCAAGC TCCCAGCATT    2640

CTTCCTTGGC TTGCAGGGAA CCAAGGTGCA AAGGTAGGAC TGAGCAGAAT CTGTTTTGGG    2700

AGACTGCAGC AAGGACCGGC AATTTTTCCA GAACAACTGT TCTTTACTTG GAAGACCTAG    2760

TTACTCCCCA TCTCTCCCTG GGACTTGCCA GGGGACCCCA GCATGGCAAC CTTAATGATG    2820

GTTCTGCTGG GTGCTAGTGG TTGCTGGCAT GCTAGTTTCT GACTCGAGAC AAATAAATTC    2880

AGATCCCTAG GGTAAGACCG GCTTCAGCAG CACCTCTCCT GACAGGGGTC CCGTCTCAGG    2940

AGAGAACTGA CTTTGTCCCA AGCAGACCTG GGCTCGGGGA ATCCTCATCA CCTCTGCAAG    3000

AGTTTTTTGT TGTTGCTGTT GTTGTGTTTT GTTGTGTTTT GTTTTTGTTT TTGATTTTTT    3060

GAAATAGAGT CTCGCTCTGA AGCCCAGGCT GGAGTGCAGT GGTGTGATCT CGGCTCACTT    3120

GCAACCTCCA CCTCCCCCAG GTTCAAGCAA TTCTCCTGCC TCAGCCTCCC AAGTAACTGG    3180

GATTACAGGC GTGCACCACC ACACCTGGAT AATTTTTCTA TTTTTAGTAG AGACAGGGTT    3240

TCACCATGTT GGCCAGGCTG GTTTCGAATT CCTGACCTCA GGTGATCCGC CCGCCTCAGT    3300

CTCCTAAAGT GTTGAGATTA CAGGCGTGAG CCACCACGCC CGGCCTGCAG GAGTCTTTAA    3360

GAGGCAGGAA CAAGGATGCA GGTGTTTCAA CAGAGAGGAA GCCTGGGGTG GGCTTCATTC    3420

CTCCTCGTGC TCTTTGCCCC CATTCACTCA GTGCTAGAGG TTGTCATTCT GCCTCTGAGA    3480

CATCCGGCCC CCTCCCTCTC CATCCCCACA CCCTCACCTG CCACAGCTGA ATCCAGGTG    3540

TGCCTCAGCT CCTGGCTGGG TACCACTGCC ACTCATCTGT AGACTCTCTA CCCTGGTGCC    3600

TTCAGGTGCC AAAGTGCATC CTCTGCCATC AGTCAAACAC ACAGTTTGAC GGATGTCACT    3660
```

```
TGCTCTGCTC AGAGACCTGC ACCGACACAG GCATGGTCAG GTTCAGGTCT TGTGGACAAG     3720

AACTGGGTCT GGAGGAGTCA GGGAAGATGT AGATGAGGAA GGTGGTACTG AAACGAACCT     3780

CTGGTACAGG GAAGATGTAC CAGGCAGCTG CAGTCACCCA GGTGAGAGAT GGTAGTCCTG     3840

GCTGGCCCAT TCTAAGTTCC AAAGCTGCCT TGGCCATCGG TCTGAGGGTG GGATGGGGGG     3900

ACATCAGAAC CAGCTGTCTC TGAGAACATA AAGGGACCCC CATATGGGAC CTCAAGACAG     3960

CTGAGCAGTC AGAGGCGCCT CTCCCGTGGC ACCAGGTCAT AGGATAATGA GACTTCTTAG     4020

AATTTCTTTC TTTTTTTTTC TTTTTTTTGA GACTGAGTCT CACTCTGTCA CCCACGCTTG     4080

AGTGCAGTGG CACTATCTAA GCTCACTGCA ACCTCCACCT CCCGGGTTCA TGTGATTCTC     4140

ATCCCTCAGT CTCCCGAGTA GCACACGCAC CATCACGCCC AGGCTAATTT TTGTATTTTT     4200

AGTAGAGAAA GGATTTTGCC ACGTTGGCCA GGCTGGTCTT CAACTCCTGA CCTCAAATGA     4260

TCTGCCCACC TCAGCCTCCC AAAGGACTAG GATTACAGGC ATGAGCCACT GTGCCTGGTC     4320

ATTCTTAGAA TTTCTGACAT TCACCATATC CGTTTGTTAG CCCCACTAAG CAAGGCTGTT     4380

TCAAATTGAC TCAGCATTTC TTATTTGTCA ATTTCTACCC CACTCCTCAC CCGGGGACTT     4440

CTGAAAACAG TGAAGGCTTC AAAGTAATCA CCTTACAAAG AAGGGCATCA TCCTCATTTC     4500

ACACATGGGG AAACTGAGGA CCACAGAGAG GAAGTAAAGA GGCCAAGGTC ACACACCTGC     4560

TACTAAGTTC CCCGTCCAGT GCTCTTTCAG CAAAAATGCA TGAGGCACAC AAGTCATGTT     4620

TCCAAACCTT CATTTCAGTA CCACCTTCAT CATTTTTGTG TTTTCCACAT AACACTTTAC     4680

TATTATTTAT GACAGGGTTT TTTTTAACCA CTCACCTTTT TTACTTATCT TTCTTTTCTT     4740

TTTCTTTAGG AGAGGCAGGA TCTCACTCTG TTGCCCAGGC TGGAGTGTAT TTCATGATCA     4800

TAGCTCACTG CAGCCTCCAA CTCCTGGGCA CACTCGATCC TCCCACTTCA GCCTCCAGAG     4860

TAGCTGGGAC TATAGTTGTG CACCATCATA CATGGCTAAT TTTTAAAAAA TCATTTGTAG     4920

AAAAATTAGC TGGATGTAGG AGAATGGCGT GAACCCAGGA GGCGGAGCTT GCAGTGAGCC     4980

AAGATAGCGC CACTGCAGTC CAGCCTGGGC GAAAGAGCGC GACTCCGTCT CAAAAAAAGA     5040

AAAAAAGAAA AGAAAAGAAA AATTAGCTGG ACATAGTGGA AGGTGCCTGT AATCCCAGCT     5100

GCTCGGGAGG CTGAGGCAGG AGAATCAGTT GAACCCAGAA CCCGGGAGGC GGAGGTTGCA     5160

GCGAGCCAAG ATCATGCCAT TGCACTCTAG CCTGGCAATA AGAGTGAAAC TCCGTCTAAA     5220

AAAAAACAAA AACAAACAAA AAAACCCCCA ACAATTTGTA GACATAGGGT GTCACTATGT     5280

TGCCCAGGCT AGCCTCCAAC TCCCGGCTTC AAGCAATCCT CCTGCTTCGG CCTCCCAAAA     5340

TGTTGGAATT ACAGGCACAA GCCACCTGGC CCAGCCATCT ACTTTATATT CAAATAAAAC     5400

TTTACGTCCC ATTATAAAGG GAAAAAATGG CAAAACAGG AGGTAACCAT TTAACAAGAA     5460

AGCAGAGTGA TGTTAGATTA TAGCAAGATA CTGTTGACTG TAGAAGGCTC TGAGGCTAGA     5520

GAGCTGCTTT CTATAAAACG GAGTGATCAT ATATTAGAAG AGGTGTTAAA GACATGTTCA     5580

CACCAAGCTG AGACTTCCTC CTTGATACCA CCAGGAGGAT GGGCAGAGAC TGGAAAAGAC     5640

ACTAACTTTC TCCCTATGGG AGTCAGTATT ATTTAGCATC ACTTTGGCGG GTCACCCCAA     5700

ACCATCTGAC TACAAGGGTA CCATATTTGG GTTAACACTC TTTTGGTATA ATTTATGTTT     5760

TAGTCCAATG TCTTGGGATG AAAATGCACAG GTGGGCCACT TATGATCTCC AGAGAAATTC     5820

AGGGCAATTT GGTGTGGGAG TAGGCATGGT AGAGGAGAGC AGCATCTAAG AAGTCCCCAG     5880

CAGAGGCTCT CAGCTTGTCT TGAGGCATCT GGGCGGAGGG CTATGATACT GGCCCCATCC     5940

TGCAGAAGGT GGCAGATATT GGCAGCTGGC ACCAGTGCGG TTCCATTGTG ATCATCATTT     6000

CTCGAACGTC AGACTGTTGA AGGTTCCCCC AACAGACTTT CTGTGCAACT TTCTGTCTTC     6060
```

```
ACCAAATTCA GTCCACAGTA AGGAAGTGAA ATTAATTTCA GAGGTGTAGG GAGGGCTTAA      6120

GGGAGTGTGG TAAAATTAGA GGGTGTTCAG AAACAGAAAT CTGACCGCTT GGGGCCACCT      6180

TGCAGGGAGA GTTTTTTTGA TGATCCCTCA CTTGTTTCTT TGCATGTTGG CTTAGCTTGG      6240

CGGGCTCCCA ACTGGTGACT GGTTAGTGAT GAGGCTGTGT GCTTCTGAGC TGGGCATCCG      6300

AAGGCATCCT TGGGGAAGCT GAGGGCACGA GGAGGGGCTG CCAGACTCCG GGAGCTGCTG      6360

CCTGGCTGGG ATTCCTACAC AATGCGTTGC CTGGCTCCAC GCCCTGCTGG GTCCTACCTG      6420

TCAGAGCCCC AAGGTAAAAA GGCCGGGAAA GCATCTTAAT TTAGCGTGCA GTCTCAGCTG      6480

GTCCTGCCAT TCCAGATAAA CAGAGAAACC ATTCTGAATT GGGGATGGGG GTGAGGATGG      6540

GAACAGGAGT CTGTGTCCTG CTGGGGCAGG CCATTGGAAG ATGTGAAAGA GTTGTCTATT      6600

TCCTTCCACC GGAGGGAGAC TTCAGGTCAG CCAGGTGTCT GGAGTATGAA CCATGTATCA      6660

GCACCGAAAG GTTCTAGA                                                    6678

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(xi) SEQUENCE DESCRIPTION: SEQ ID NO:2:

GCTGCCTGGC TGGGATTCCT A                                                  21

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(xi) SEQUENCE DESCRIPTION: SEQ ID NO:3:

CCTCCCTGGT CTCTTCATCA C                                                  21

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA oligonucleotide"

(xi) SEQUENCE DESCRIPTION: SEQ ID NO:4:

AGGATGCCTT CGGATGCCCA GCTCAGAAGC                                         30
```

REGULATORY GENETIC DNA THAT REGULATES THE CLASS II TRANSACTIVATOR (CIITA)

STATEMENT OF FEDERAL SUPPORT

This invention was made with Federal support under Grant Number 5-RO1-CA48185 from the National Institutes of Health. The government has certain rights to this invention.

FIELD OF THE INVENTION

The present invention relates to DNA regulatory elements that control expression of the Class II Transactivator (CIITA) gene. In addition, the present invention discloses assay systems for identifying compounds that alter major histocompatability (MHC) antigen gene expression.

BACKGROUND OF THE INVENTION

The class II major histocompatibility (MHC) antigens play a critical role in regulating the cellular immune response. In particular, the appropriate constitutive and inducible expression of class II MHC molecules are essential for normal immune response, whereas aberrantly high or low expression has been correlated with various autoimmune diseases (Massa et al., *Proc. Natl. Acad. Sci USA* 84, 4219–4223 (1987)) and a type of severe combined immunodeficiency disease (SCID) known as the Bare Lymphocyte Syndrome (BLS) (Griscelli et al., *Immunodeficiency Rev.* 1, 135–53 (1989)). Additionally, the class II MHC antigens are known to play a crucial role in causing organ transplant rejections.

Recognition of class II MHC by self T cells is a crucial step in most cell-mediated immunity. The process by which class II MHC antigens are recognized by T cells is called antigen presentation. Antigen presentation requires both the structural proteins, class II MHC molecules, which form the actual transplantation antigens recognized by the T cells, and molecules that are necessary for the targeting and proper function of class II MHC molecules (the li and DMA/DMB molecules).

The primary regulation of both constitutive and interferon-γ (IFN-γ)-induced class II MHC antigen gene expression occurs at the transcriptional level. Figueiredo et al., *J. Immunol.* 143, 3781–3786 (1989). Expression of the recently identified MHC class II transactivator, CIITA, closely parallels class II MHC antigen gene expression. Steimle et al., *Cell* 75, 135–46 (1993). It has also been shown that CIITA is induced by IFN-γ, and transfection of CIITA alone into cells is sufficient to activate class II MHC, li, and DM genes. See, e.g., Chin et al., *Immunity* 1, 679 (1994); Chang et al., *J. Exper. Med.* 180, 1367–1374 (1994); Steimle et al., *Science* 265, 106–08 (1994). CIITA transcript is expressed constitutively in class II MHC-positive cells; however, it can be induced in certain cell types such as fibroblasts, macrophages, and glioblastoma cells upon treatment with IFN-γ. See Chang et al., supra; Steimle et al. (1994), supra, 106–08. The kinetics of CIITA induction by IFN-γ precedes the induction of class II MHC transcripts, and introduction of CIITA alone into a number of cell types is sufficient to activate class II MHC antigen genes.

The N-terminus of the CIITA protein contains an acidic domain (amino acids 30–160), followed by domains rich in proline (amino acids 163–195), serine (amino acids 209–257), and threonine (amino acids 260–322). Steimle et al., 1993, supra. An acidic domain has been found in many transcription factors and has been shown to interact with basal transcriptional machinery in vitro and in vivo. See, e.g., Schmitz et al., *J. Biol. Chem.* 270, 7219–7226 (1995); Tong et al., *Proc. Natl. Acad. Sci. USA* 92, 3259–3263 (1995). However, it is likely that the acidic domain alone is not sufficient to activate the class II MHC promoter in CIITA, and that the acidic domains of other transcription factors behave differently from the CIITA acidic domain. Zhou et al., *Immunity* 2, 545–553 (1995). Analysis of the primary amino acid sequence of CIITA does not show any homology to known conserved DNA-binding motif of transcription factors, and in vitro translated CIITA apparently does not interact with DNA. Steimle et al. (1993), supra.

CIITA is now recognized as a "master control" molecule that transactivates all class II MHC genes, as well as genes necessary for the function of class II MHC molecules. In total, CIITA regulates at least seventeen genes, all of which are involved in immune activation. Because CIITA plays a central role in inducing expression of the class II MHC genes and orchestrating helper T cell activation, CIITA is implicated in the etiology of AIDs, transplant rejection, and autoimmune disease states (e.g., lupus, arthritis, diabetes, and multiple sclerosis). Accordingly, the present invention responds to a need in the art for improved methods of modulating immune responsiveness, in particular class II MHC antigen expression and helper T cell activation.

SUMMARY OF THE INVENTION

The present invention discloses the identification of novel DNAs, which control the expression of a master molecule, the Class II transactivator (CIITA). CIITA regulates at least seventeen genes, all involved in immune activation. The DNAs provided by the present investigations can be used to identify compounds that modulate CIITA expression, and thereby alter class II MHC-associated molecules and functions.

Accordingly, a first aspect of the present invention is isolated DNAs comprising the Class II Transactivator regulatory element.

A second aspect of the present invention is recombinant DNA comprising a Class II Transactivator regulatory element operably associated with a heterologous DNA. The present invention further provides cells containing the disclosed recombinant DNAs.

A third aspect of the present invention is an assay for identifying compounds that regulate class II major histocompatibility (MHC) antigen expression, comprising: contacting a test compound to a cell containing a heterologous DNA, as described hereinabove; and then detecting a change in the transcription of the heterologous DNA, a change in transcription indicating the compound has class II MHC regulatory activity.

A fourth aspect of the present invention is a compound that regulates class II major histocompatibility (MHC) antigen expression, the compound identified by an assay comprising: contacting a test compound to a cell containing an isolated DNA comprising a recombinant DNA comprising a class II transactivator regulatory element operably associated with a heterologous DNA; and then detecting a change in the transcription of said heterologous DNA, a change in said transcription indicating said compound has class II MHC regulatory activity.

The foregoing and other objects and aspects of the present invention are explained in detail in the drawings herein and the specification set forth below.

BRIEF DESCRIPTION OF THE DRAWINGS

FIGS. 2A–C. Localization of the 5' UTR, exon 1, and the transcription start site of the CIITA gene in the genomic CIITA clone 10.

FIG. 2A. Map of the human genomic CIITA clone 10. The 5' UTR oligonucleotide hybridizes to an Xba I fragment of approximately 6.7 kb. The location of the region that hybridizes to this probe is marked with an arrow.

FIG. 2B. Restriction map of the 6678 bp Xba I fragment of FIG. 2A containing the 5' UTR of the CIITR gene. The full nucleotide sequence of this fragment is presented in SEQ ID NO:1.

FIG. 2C. DNA sequence of the Kpn I-Xba I fragment (see FIG. 2B—nucleotides 5720 to 6678 of SEQ ID NO:1) surrounding the first exon of the human CIITA gene. Exon I sequences are underlined. The 3' end of exon 1 of the human CIITA gene was determined by a comparison of the genomic DNA sequence to the sequence of the human CIITA cDNA (Steimle et al. *Cell* 75, 135–46 (1993)), and the 5' end of exon 1 was determined by mapping the transcriptional start site by primer extension as described in Example 3. The oligonucleotide used in the primer extension was the reverse complement of the sequences designated underlined by an arrow. The end of the human CIITA cDNA that has been reported by Steimle et al. is marked by an arrowhead. The start site of transcription is marked with an asterisk. Restriction enzyme sites used in cloning and preparation of constructs for transfection are double underlined.

FIG. 7A. The luciferase activity of p6374CIITA.Luc and pDR.Luc are not activated in U3A cells in response to IFN-γ. Transient transfections of STAT1 defective U3A cells were performed by calcium phosphate co-precipitation. Cells were plated in 10 cm dishes at a density of $5 \times 10^5$ cells 24 hr prior to transfection. Ten µg of reporter construct was added to each dish of cells. After 6 hr, the precipitates were removed, dishes were rinsed with PBS, and 10 ml of culture medium was added with or without 500 U/ml of recombinant human IFN-γ. Cells were harvested for luciferase assays 14 hr later. The pDR.Luc reporter construct contains the proximal promoter sequences of the class II MHC gene HLA-DRα. This experiment has been repeated once with p6374CIITA.Luc and once with p-2158CIITA.Luc with similar results.

FIG. 7B. Over-expression of STAT1 in the STAT1 defective cell line, U3A, stimulates the induction of p6374CIITA.Luc and pDR.Luc in response to IFN-γ. Transient transfections of STAT1 defective U3A cells were performed by calcium phosphate co-precipitation. Cells were plated in 10 cm dishes at a density of $5 \times 10^5$ cells 24 hr prior to transfection. Ten µg of reporter construct in combination with 10 µg of either the STAT1 expression vector or the empty pCDNA3 vector were added to each dish of cells. After 6 hr, the precipitates were removed, dishes were rinsed with PBS, and 10 ml of culture medium was added with or without 500 U/ml of recombinant human IFN-γ. Cells were harvested for luciferase assays 14 hr later. The empty pCDNA3 vector was used as a negative control.

Figure 1:
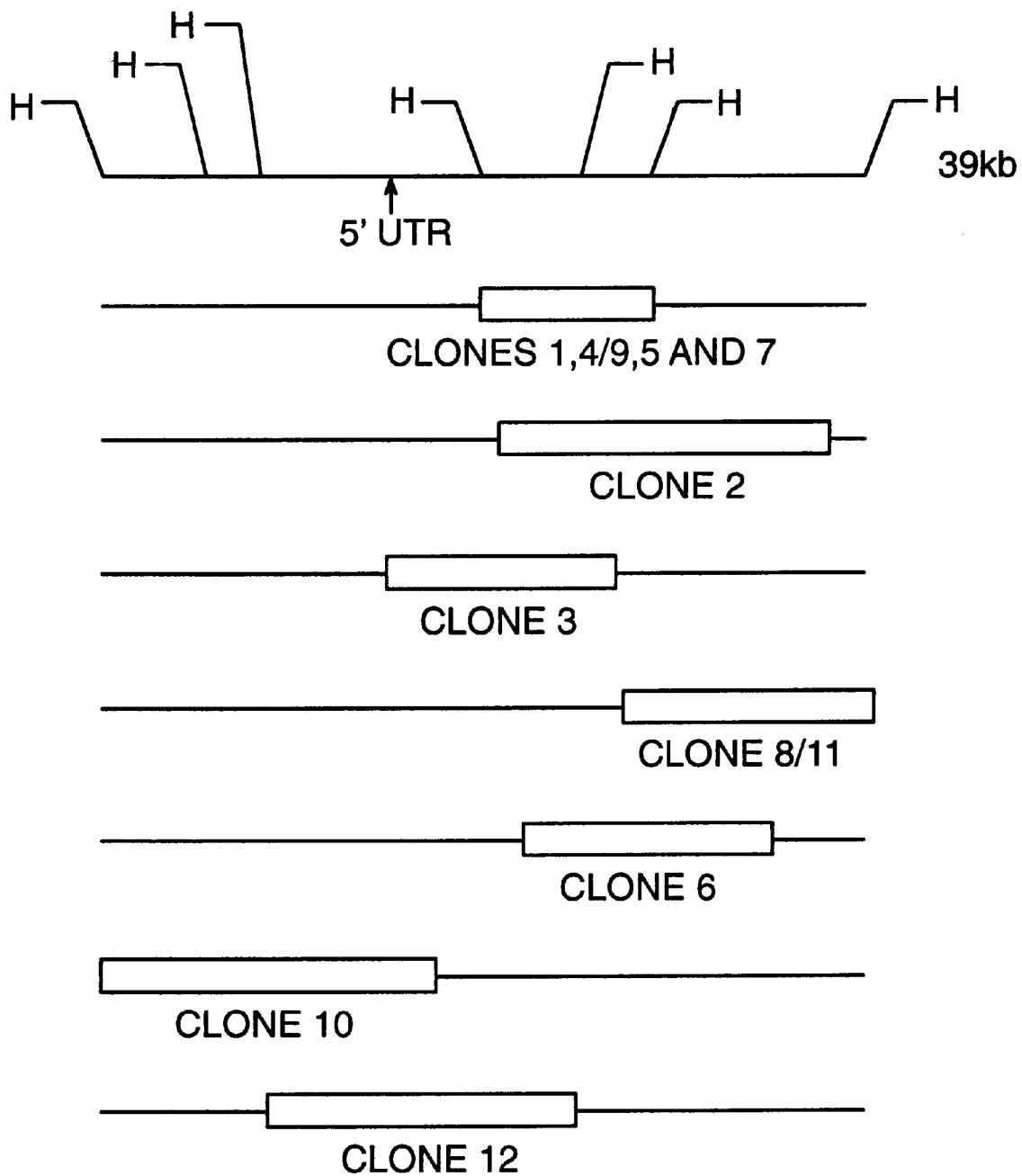
FIG. 1. Map of the genomic DNA contained in the twelve isolated human CIITA clones showing the relative location of each clone. DNA was digested with Hind III and analyzed by Southern blotting. The top diagram is a map of the 39 kb region of human genomic DNA spanned by the twelve clones: (H) Hind III. The approximate location of the region hybridizing to the 5' UTR oligonucleotide is marked with an arrow. The location of each clone is designated by a box. Individual members of the pairs of clones designated 4/9 and 8/11 are identical or nearly identical. Clones 10 and 12 (grey boxes) were chosen for additional Southern blot analyses localizing the 5'-flanking region of the human CIITA gene.

The pDR.Luc reporter construct which contains the proximal promoter sequences of the class II MHC gene HLA-DRα was used as a positive control. The presence or absence of plasmids in the transfection is indicated by plus and minus symbols, respectively. This is a representative experiment of three independent experiments which all show the stimulatory effect of over-expression of STAT1 on IFN-γ induction of p6374CIITA.Luc. This experiment has also been repeated with p-2158CIITA.Luc with similar results.

DETAILED DESCRIPTION OF THE INVENTION

Nucleotide sequences are presented herein by single strand only in the 5' to 3' direction, from left to right. Nucleotides are represented herein in the manner recommended by the IUPAC-IUB Biochemical Nomenclature Commission, in accordance with 37 CFR §1.822 and established usage. See, e.g., UNITED STATES PATENT AND TRADEMARK OFFICE, PATENTIN USER MANUAL, 99–102 (Nov. 1990).

In describing the present invention, "SDS" means sodium dodecyl sulfate, "SSC" means sodium chloride/sodium citrate, "SSPE" means sodium chloride/sodium phosphate/ethylene diamine tetraacetate, "PBS" means phosphate-buffered saline, "DMSO" means dimethyl sulfoxide, "cm" means centimeter, "mm" means millimeter, "ml" means milliliter, "$\mu$l" means microliter, "M" means molar, "mM" means millimolar, "mmol" means millimole, "$\mu$g" means microgram, "ng" means nanogram, "U" means unit, "Ci" means Curie, "bp" means base pair, "kb" means kilobase pair, "nt" means nucleotide, "hr" means hour, "mV" means millivolt, and "$\mu$F" means microFarad.

A. DNA Sequences:

The isolated DNAs of the present invention encode regulatory elements for the Class II Transactivator (CIITA) gene. A DNA "regulatory element" as used herein is any DNA sequence that regulates gene expression at the transcriptional level (i.e., activates and/or suppresses). A "Class II Transactivator regulatory element" (CIITA regulatory element) is a DNA sequence that regulates transcription of the CIITA gene. The CIITA regulatory elements disclosed herein that activate transcription of the CIITA gene, increase CIITA gene transcription by at least 50%, more preferably by at least 100%, 150%, 200%, or even 300%, or more. CIITA regulatory elements disclosed herein that suppress CIITA gene transcription do so by at least 25%, more preferably by at least 35%, 50%, 60%, 75%, or even 85%, or more.

The CIITA regulatory elements of the present invention are located within the approximately 6.4 kb of flanking DNA of the CIITA gene (nucleotides 1 to 6374 of the 6678 bp Xba I fragment of SEQ ID NO:1). This approximately 6.4 kb DNA fragment is primarily comprised of flanking genomic DNA, but it also includes 112 bp of 5' UTR of the CIITA gene (see FIGS. 2A–C). It will be apparent that other sequence fragments from the human CIITA 5' flanking region, longer or shorter than the foregoing sequence, or with minor additions, deletions, or substitutions made thereto, can be prepared which will also carry the CIITA regulatory element, all of which are included within the present invention.

The isolated DNAs comprising the CIITA regulatory elements can be from any species of origin, including mouse, rat, rabbit, cat, porcine, and human, but are preferably of mammalian origin. In one preferred embodiment of the invention, the isolated DNA encoding the CIITA regulatory element has the sequence given as SEQ ID NO:1. In other preferred embodiments, the sequence of the isolated DNA encoding the CIITA regulatory element corresponds to a continuous segment of DNA within the DNA given as SEQ ID NO:1, including but not limited to the continuous segment given as nucleotides 1 to 3562 of SEQ ID NO:1, and the continuous segment given as nucleotides 1 to 2182 of SEQ ID NO:1. CIITA regulatory elements of the present invention include DNA molecules that regulate expression of the CIITA gene and have sequences that are substantially homologous to the DNA sequences comprising the CIITA regulatory elements disclosed herein, and particularly the human CIITA regulatory element disclosed herein as SEQ ID NO:1. CIITA regulatory elements of the present invention also encompass DNA molecules that regulate expression of the CIITA gene and have sequences that are substantially homologous to continuous segments of DNA located within SEQ ID NO:1, including but not limited to the continuous segment given as nucleotides 1 to 3562 of SEQ ID NO:1, and the continuous segment given as nucleotides 1 to 2182 of SEQ ID NO:1. This definition is intended to include natural allelic variations in the DNA sequence comprising the CIITA regulatory element. As used herein, regions that are "substantially homologous" are at least 75%, and more preferably are 80%, 85%, 90% or even 95% homologous.

CIITA regulatory elements from other species include those which are at least about 75 percent homologous (and more preferably 80%, 85%, 90% or even 95% homologous) to the human CIITA regulatory elements disclosed herein, in particular the CIITA regulatory element having the sequence given herein as SEQ ID NO:1 and which are capable of regulating the transcription of the CIITA gene. CIITA regulatory elements from other species also include those which are at least about 75 percent homologous (and more preferably 80%, 85%, 90% or even 95% homologous) to a continuous segment of the CIITA regulatory elements as defined herein as SEQ ID NO:1, and which are capable of regulating the transcription of the CIITA gene, including but not limited to the continuous segment given herein as nucleotides 1 to 3562 of SEQ ID NO:1, and the continuous segment given herein as nucleotides 1 to 2182 of SEQ ID NO:1.

High stringency hybridization conditions which will permit homologous DNA sequences to hybridize to a DNA sequence as given herein are well known in the art. For example, hybridization of such sequences to DNA disclosed herein may be carried out in 25% formamide, 5×SSC, 5×Denhardt's solution, with 100 $\mu$g/ml of single stranded DNA and 5% dextran sulfate at 42° C., with wash conditions of 25% formamide, 5×SSC, 0.1% SDS at 42° C. for 15 minutes, to allow hybridization of sequences of about 60% homology. More stringent conditions are represented by a wash stringency of 0.3M NaCl, 0.03 M sodium citrate, 0.1% SDS at 60° or even 70° C. using a standard in situ hybridization assay. (See SAMBROOK ET AL., MOLECULAR CLONING, A LABORATORY MANUAL (2d ed. 1989)). In general, DNA sequences which comprise CIITA regulatory elements and which hybridize to the DNA comprising the CIITA regulatory elements disclosed herein will be at least 75%, 80%, 85%, 90% or even 95% homologous or more with the DNA sequences of the CIITA regulatory elements disclosed herein.

Knowledge of the nucleotide sequence of the CIITA regulatory elements disclosed herein can be used to generate hybridization probes which specifically bind to the 5' flanking genomic DNA of the CIITA gene to determine the presence of this region of genomic DNA, by Southern hybridization for example. Probes also serve as primers for use in amplifying the CIITA gene, or portions thereof, by polymerase chain reaction (PCR) in accordance with the process described in U.S. Pat. Nos. 4,683,202 and 4,683,195. All United States patent references cited herein are intended to be incorporated in their entirety by reference.

The CIITA regulatory elements provided by the present invention interact with transcription factors to regulate transcription of the CIITA gene. Regulation of transcription refers to altering or modulating (i.e., activating or suppressing) the level of transcription. The DNA regulatory elements can also interact with other regulatory factors or intracellular signalling molecules so as to effect changes in gene transcription. Alternatively, the transcription factor, regulatory factor, or intracellular signalling molecule may alter CIITA gene transcription by interacting with DNA binding proteins that are bound to the CIITA regulatory element and only secondarily with the CIITA regulatory element itself.

In one preferred embodiment of the invention, the isolated CIITA regulatory element comprises an interferon-γ (IFN-γ) responsive regulatory element, such that the CIITA regulatory element modulates (i.e., activates or suppresses) transcription of the CIITA gene in response to cellular stimulation by IFN-γ. In another preferred embodiment, the isolated DNA comprises a transforming growth factor-β (TGF-β) responsive regulatory element. In other preferred embodiments, the isolated DNA comprises a tumor necrosis factor-α (TNF-α) responsive regulatory element, an interferon-α (IFN-α) responsive regulatory element, an interferon-,β (IFN-β) responsive regulatory element, an interleukin-1 (IL-1) responsive regulatory element, an interleukin-4 (IL-4) responsive regulatory element, a dexamethasone (or other glucocorticoid) responsive regulatory element, a glutamate responsive regulatory element, a cAMP agonist responsive regulatory element, or a granulocyte-macrophage-CSF responsive regulatory element. Alternatively, the CIITA regulatory elements are responsive to steroid hormones, protein hormones, growth factors, neurotransmitters, and cytokines (including monokines and lymphokines).

The present invention also provides recombinant DNAs comprising a CIITA regulatory element operably associated with heterologous DNA. The CIITA regulatory element is operably associated with the heterologous DNA such that the CIITA regulatory element is functionally linked to the heterologous DNA, and can thereby alter transcription of the heterologous DNA. Typically, the CIITA regulatory element will be located 5' to the heterologous DNA, but it may also be located 3' to the heterologous DNA as long as it is operably associated therewith. There are no particular upper or lower limits as to the distance between the CIITA regulatory element and the heterologous DNA, as long as the two DNA segments are operably associated with each other.

The heterologous DNA segment may encode any protein or peptide which is desirably expressed by the host cell. Typically, the heterologous DNA includes regulatory segments necessary for the expression of the protein or peptide in the host cell (i.e, promoter elements). Suitable heterologous DNA may be of prokaryotic (e.g., DNA encoding the Botulinus toxin C), or eukaryotic (e.g., DNA encoding firefly luciferase) origins. Illustrative proteins and peptides encoded by the heterologous DNAs of the present invention include enzymes, hormones, growth factors, and cytokines. Preferably, the heterologous DNA encodes a reporter protein, described in more detail hereinbelow, such as β-galactosidase, *Escherichia coli* (*E. coli*) chloramphenicol acetyltransferase (CAT), firefly luciferase, or the green fluorescent protein (GFP) of the jellyfish *Aequorea victoria*. In another preferred embodiment of the invention, the heterologous DNA encodes growth hormone (i.e., somatotropin).

Alternatively, the heterologous DNA can be used to express antisense RNAs. In general, "antisense" refers to the use of small, synthetic oligonucleotides to inhibit gene expression by inhibiting the function of the target mRNA containing the complementary sequence. Milligan, J. F. et al., *J. Med. Chem.* 36(14), 1923–1937 (1993). Gene expression is inhibited through hybridization to coding (sense) sequences in a specific mRNA target by hydrogen bonding according to Watson-Crick base pairing rules. The mechanism of antisense inhibition is that the exogenously applied oligonucleotides decrease the mRNA and protein levels of the target gene. Milligan, J. F. et al., *J. Med. Chem.* 36(14), 1923–1937 (1993). See also Helene, C. and Toulme, *J., Biochim. Biophys. Acta* 1049, 99–125 (1990); Cohen, J. S., Ed., OLIGODEOXYNUCLEOTIDES AS ANTISENSE INHIBITORS OF GENE EXPRESSION, CRC Press:Boca Raton, Fla. (1987).

C. Genetic Engineering Techniques.

The production and use of cloned genes, recombinant DNA, vectors, transformed host cells, selectable markers, proteins, and protein fragments by genetic engineering are well-known to those skilled in the art. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col 3 line 26 to Col 14 line 12; and U.S. Pat. No. 4,879,224 to Wallner at Col. 6 line 8 to Col. 8 line 59.

A vector is a replicable DNA construct. Vectors are used herein to amplify DNA encoding the CIITA regulatory elements as given herein or recombinant DNA as given herein. Alternately, vectors are used herein to express DNA comprising the heterologous DNAs as given herein.

An expression vector is a replicable DNA construct in which a DNA sequence encoding a protein is operably linked to suitable control sequences capable of effecting the expression of proteins. The need for such control sequences will vary depending upon the host selected and the transformation method chosen. Generally, control sequences include a transcriptional promoter, an optional operator sequence to control transcription, RNA intron splice sites (if intron-containing genomic DNA is used), a sequence encoding suitable mRNA ribosomal binding sites, and sequences which control the termination of transcription and translation.

Suitable control sequences may vary according to the function of the particular expression vector. For some purposes it is preferable to have an expression vector with a constitutive promoter. In other instances, it is preferable to have an expression vector with an inducible promoter. For example, as described hereinbelow, it is often desirable to use inducible promoters to identify compounds that stimulate CIITA gene expression. One can also use inducible promoters to identify compounds that suppress the induction of gene expression by another compound. As a further alternate, it is sometimes advantageous to use constitutive promoters to identify compounds that suppress CIITA gene expression.

Amplification vectors do not require expression control domains. All that is needed is the ability to replicate in a host, usually conferred by an origin of replication, and a selection gene to facilitate recognition of transformants.

Reporter vectors comprise a sub-class of expression vectors. Reporter vectors are used herein to introduce a reporter gene into the host cell. The protein encoded by the reporter gene should not normally be present in the host cell. Expression of a reporter gene confers an easily-detectable phenotype on the host cell.

Reporter genes compatible with various host cell systems are known. Reporter genes useful in yeast cells include those containing the HIS3, LEU2, or TRP1 genes. These reporter vectors are used in conjunction with host yeast strains that are deficient in endogenous HIS3, LEU2, or TRP1 function, respectively. The herpes viral thymidine kinase gene can also be employed as a reporter in yeast cells. In higher eukaryote host cells the *E. coli* chloramphenicol acetyltransferase (CAT) and firefly luciferase genes are examples of commonly-used reporter genes. There is little or no background activity for these enzymes in the commonly-employed higher eukaryotic host cell systems. More recently, the green fluorescent protein (GFP) of the jellyfish *Aequorea victoria* has been used as a reporter gene in a wide variety of microbial, plant, insect and mammalian cells. GFP is a species-independent reporter that requires no substrate in order to fluoresce. A. Crameri et al., *Nature Biotech.* 14, 315–319 (1996). Other reporter gene systems compatible with these and other host cell systems are well known to those skilled in the art.

Vector DNA generally replicates and functions independently of the host genome, but may, in some instances, integrate into the genome itself. Suitable vectors for practicing the present invention include plasmids, viruses (e.g., adenovirus, cytomegalovirus), phage, retrovirus and integrated DNA fragments (i.e., fragments integratable into the host genome by recombination). In a preferred embodiment of the invention, plasmid vectors are used to transform host cells. Expression vectors should contain a promoter and RNA binding site which are operably linked to the gene to be expressed.

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with vectors containing DNA comprising CIITA regulatory elements or recombinant DNA as given hereinabove. Transformed host cells ordinarily express protein, but host cells transformed for purposes of cloning or amplifying DNA need not express protein.

Transfection may be carried out by any suitable means, such as methods employing liposomes, microinjection, cell fusion, DEAE-dextran, calcium phosphate precipitation, electroporation, microparticle bombardment, conjugation into a complex internalized into a cell (see, e.g., D. Curiel et al., U.S. Pat. No. 5,521,291), and other techniques known to those skilled in the art. The term co-transfection, as used herein, indicates transfection of host cells with more than one vector, such that the host cell contains at least one copy of each of the transfected vectors. Said multiple transfections need not be carried out simultaneously, but may instead be performed sequentially over time.

The invention disclosed herein provides cells containing recombinant DNA encoding a CIITA regulatory element operably associated with a heterologous DNA, as described hereinabove. Cells of the present invention can be of prokaryotic, lower eukaryotic (e.g., yeast) or higher eukaryotic origin, preferably of higher eukaryotic origin, more preferably of mammalian origin. Culturing of host cells may be carried out by any suitable technique. Prokaryote host cells include gram negative or gram positive organisms, for example *E. coli* or Bacilli. Higher eukaryotic cells can be primary or serially-passaged cultures of cells, transformed cells, or established cell lines. Mammalian cells can be of any cell type in which it would be desirable to express the recombinant DNAs of the present invention.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cells in culture include, but are not limited to: B and T lymphocytes, Kupffer cells, lymphoma cells, dendritic cells, astrocytes, intestinal and colonic epithelial cells, macrophages, monocytes, glioblastoma cells, endothelial cells, Langerhans cells, fibroblasts, and microglia cells (including their transformed counterparts). Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Rather than using vectors which contain viral origins of replication, one can transform mammalian cells by the method of co-transformation with a selectable marker and a recombinant DNA encoding a CIITA regulatory element operably associated with a heterologous DNA, as described hereinabove. An example of a suitable selectable marker is dihydrofolate reductase (DHFR) or thymidine kinase. See U.S. Pat. No. 4,399,216. Such markers are proteins, generally enzymes, that enable the identification of transformant cells. Generally, identification is by survival of transformants in culture medium that is toxic, or from which the cells cannot obtain critical nutrition without having taken up the marker protein.

Other methods for adaptation to the expression of recombinant DNA, as given herein, in recombinant vertebrate cell culture include those described in M-J. Gething et al., *Nature* 293, 620 (1981); N. Mantei et al., *Nature* 281, 40; A. Levinson et al., EPO Application Nos. 117,060A and 117,058A.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV,

*Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

A broad variety of suitable prokaryotic and microbial vectors are available. See J. SAMBROOK ET AL., MOLECULAR CLONING: A LABORATORY MANUAL (2d ed. 1989). pBR322 or a plasmid derived therefrom is often used to transform *E. coli.* See Bolivar et al., *Gene* 2, 95 (1977). Promoters commonly used in recombinant microbial expression vectors include the beta-lactamase (penicillinase) and lactose promoter systems (Chang et al., *Nature* 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc Natl. Acad. Sci. USA* 80, 21 (1983)). While these are commonly used, other microbial promoters are suitable. Details concerning nucleotide sequences of many have been published, enabling a skilled worker to operably ligate them to DNA encoding the protein in plasmid or viral vectors (Siebenlist et al., *Cell* 20, 269 (1980)).

Eukaryotic microbes such as yeast may be transformed with suitable protein-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). This plasmid contains the trpl gene, which provides a selection marker for a mutant strain of yeast lacking the ability to grow in tryptophan, for example ATCC No. 44076 or PEP4–1 (Jones, *Genetics* 85, 12 (1977)). The presence of the trpl lesion in the yeast host cell genome then provides an effective environment for detecting transformation by growth in the absence of tryptophan.

Suitable promoting sequences in yeast vectors include the promoters for metallothionein, alcohol dehydrogenase, adenylate cyclase, 3-phosphoglycerate kinase (Hitzeman et al., *J. Biol. Chem.* 255, 2073 (1980), and other glycolytic enzymes (Hess et al., *J. Adv. Enzyme Reg.* 7, 149 (1968); and Holland et al., *Biochemistry* 17, 4900 (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

D. Screening Assays

The CIITA protein is essential for the expression of fourteen different genes that code for class II transplantation molecules as well as the li and DMA/DMB molecules necessary for antigen processing. This transactivator is highly specific and is not likely to interfere with the expression of many other genes necessary for cell survival since cells without this gene can grow and differentiate normally, although they cannot elicit a T cell response. This high level of specificity is rare among transactivators.

Accordingly, the CIITA regulatory elements disclosed herein find use as the basis of a rapid screening assay for compounds that regulate the expression of CIITA, and hence all class II MHC antigen expression. The present investigations have identified CIITA regulatory elements that modulate transcription of the CIITA gene in response to IFN-γ and TGF-β. Other compounds can be screened for those that regulate CIITA gene transcription through the CIITA regulatory elements disclosed herein. The screening assay comprises contacting a test compound to a cell containing a recombinant DNA encoding a CIITA regulatory element operably associated with a heterologous DNA, and then detecting a change in the transcription of said heterologous DNA. A change in transcription of the heterologous DNA is an indicator that the test compound regulates (i.e., activates or suppresses) CIITA gene transcription. Activating compounds according to this embodiment of the invention will activate CIITA gene transcription by at least 50%, more preferably by at least 100%, 150%, 200%, or even 300%, or more. Suppressing compounds according to this embodiment of the invention will suppress CIITA gene transcription by at least 25%, more preferably by at least 35%, 50%, 60%, 75%, or even 85%, or more.

The term "compound" as used herein is construed broadly and includes, but is not limited to, any naturally-occurring or synthetic element, chemical group, or molecule. Organic compounds (i.e., those containing at least one carbon) are preferred (e.g., cAMP, amino acids, ketones, acids, amides, amines, esters, nucleotides and their derivatives, thiols, ethers, lipids, heterocyclic ring systems, and adenine derivatives). Other preferred compounds include steroid hormones, protein hormones, growth factors, neurotransmitters, and cytokines (including monokines and lymphokines). In one particular embodiment of the invention, the compound is TGF-β, preferably TGF-β1. In other preferred embodiments, the compound is TNF-α, IFN-α, IFN-β, IL-1, IL-4, dexamethasone (or other glucocorticoid), glutamate, a cAMP agonist, or granulocyte-macrophage-CSF. A compound can control the activity of the CIITA regulatory elements disclosed herein either directly or indirectly, as described in more detail hereinbelow.

Some cell types exhibit constitutive expression of the CIITA gene (i.e., the CIITA gene is always expressed), whereas in other cell types expression of CIITA is inducible (i.e., the CIITA gene is not normally expressed, but is induced or "turned on" in response to an external factor). Examples of cell types that constitutively express CIITA include B lymphocytes, lymphoma cells, and dendritic cells. In contrast, astrocytes, macrophages, monocytes, glioblastoma cell lines, endothelial cells, Langerhans cells, fibroblasts and microglia cells show inducible expression of CIITA. In one embodiment of the invention, cells that exhibit inducible expression of CIITA are used to identify compounds that activate or enhance CIITA gene transcription (e.g., IFN-γ). In another embodiment, cells that show inducible expression of CIITA are used to identify compounds that suppress the induction of CIITA gene expression by another compound (e.g., TGF-β suppresses IFN-γ induced CIITA gene expression). In a further alternate embodiment of the invention, cells that exhibit constitutive expression of CIITA are used to identify compounds that suppress CIITA gene transcription.

The step of detecting or measuring a change in transcription of the heterologous DNA can be carried out by any suitable technique. Typically, the heterologous DNA will encode an easily detectable reporter protein, as described hereinabove. Any reporter molecule that is expressed and easily detected is satisfactory for use in carrying out the screening assay. Exemplary reporter molecules include, but are not limited to, the *E. coli* chloramphenicol acetyltransferase (CAT), firefly luciferase, and the green fluorescent protein (GFP) of the jellyfish *Aequorea victoria*.

Recombinant DNA encoding the CIITA regulatory element operably associated with heterologous DNA can be constructed by any suitable technique known in the art. A test compound is contacted with a cell containing the above-described recombinant DNA. Those skilled in the art will appreciate that test compounds can be contacted with cells containing the recombinant DNA by any suitable technique. The test compounds can simply be added to the culture medium in which the cells are growing. Alternatively, test compounds can be expressed from a second recombinant DNA that is co-transfected into the cell. As a further alternative, test compounds may be peptides or proteins expressed from a combinatorial library cotransfected into the cell.

The screening assay identifies test compounds that activate or suppress the CIITA regulatory element so as to activate or suppress transcription of the heterologous DNA. Compounds that alter transcription of the heterologous DNA are characterized as exhibiting "class II MHC regulatory activity." Compounds that activate CIITA gene transcription will activate by at least 50%, more preferably by at least 100%, 150%, 200%, or even 300%, or more. Compounds that suppress CIITA gene transcription will suppress by at least 25%, more preferably by at least 35%, 50%, 60%, 75%, or even 85%, or more. The basic premise underlying the screening assay is that the expression of class II MHC genes is regulated at the transcriptional level, and CIITA regulates the transcription of all class II MHC genes. Thus, compounds identified as controlling CIITA gene expression by the screening assay disclosed herein are excellent candidates for molecules that regulate the entire complement of class II MHC genes in vivo.

While not wishing to be held to any particular theory of the invention, it is envisioned that some class II MHC regulatory compounds will not interact directly with the DNA comprising the CIITA regulatory element. Instead, these compounds may trigger the synthesis or activation of intracellular signalling molecules or transcription factors that will interact directly with the CIITA regulatory element or with other compounds bound thereto as described hereinabove (i.e., such a model has been proposed for the intracellular actions of protein hormones). Alternatively, some class II MHC regulatory compounds will interact directly with the CIITA regulatory element or other compounds bound thereto as described hereinabove (i.e., such a model has been proposed for the intracellular actions of steroid hormones).

This screening assay is advantageous because CIITA expression is reflective of the expression of all genes known to exist in the class II MHC pathway as well as functional genes necessary for the execution of this pathway. Using the CIITA regulatory element in a screening assay, large numbers of compounds can be rapidly tested for activity in regulating class II MHC expression and function, either down-regulation (which may be beneficial for autoimmunity, inflammatory diseases, and transplantation) or up-regulation (which may be beneficial for immunodeficiencies, including AIDS, and cancer therapy).

The following Examples are provided to more fully illustrate the present invention, and are not to be construed as limiting thereof.

EXAMPLE 1

Cell Lines

Raji is a human Epstein-Barr virus-transformed Burkitt's lymphoma cell line grown in RPMI 1640 supplemented with 8% fetal calf serum, 2 mM L-glutamine and 100 U/ml penicillin and streptomycin. U373-MG is a human glioblastoma multiforme line which expresses class II MHC molecules after treatment with IFN-γ. Basta et al., *J. Immunol.* 138, 1275–80 (1987). U373MG is grown in McCoy's 5A medium supplemented with 10% fetal calf serum (FCS), 2 mM L-glutamine and 100 U/ml penicillin and streptomycin. U3A (generously provided by Dr. George Stark, Cleveland Clinic Foundation Research Institute, Cleveland, Ohio) is a STAT1 defective cell line derived from 2FTGH. Pellegrini et al., *Mol. Cell. Biol.* 9, 4605–12 (1989). U3A cells were maintained in Dulbecco's Modified Eagle Medium (Life Technologies) supplemented with 10% FCS, 2 mM L-glutamine, and 100 U/ml penicillin and streptomycin. RAW 264.7 murine macrophage cells were grown in RPMI 1640 (Life Technologies) supplemented with 10% FCS, 2 mM L-glutamine, and 100 U/ml penicillin and streptomycin.

EXAMPLE 2

Isolation and Characterization of Human CIITA Genomic Clones

To isolate genomic clones containing the 5'-flanking region of the human CIITA gene, approximately one million recombinants from a commercially prepared λFIX II human fibroblast genomic library (Catalog #946204, Stratagene, La Jolla, Calif.) were screened as previously described. Piskurich et al., *J. Immunol.* 154, 1735–47 (1995). The probe was simultaneously amplified and radiolabeled using PCR (Perkin-Elmer Cetus, Norwalk, Conn.) in the presence of [$^{32}$P]-dCTP (Dupont, NEN Research Products, Boston, Mass.). Oligonucleotide primers used for the PCR correspond to nt 91 to 111 (5' GCTGCCTGGCTGGGATTCCTA 3'—SEQ ID NO:2) and the reverse compliment of nt 375 to 395 (5' CCTCCCTGGTCTCTTCATCAC 3'—SEQ ID NO:3) of the human CIITA cDNA sequence as reported by Steimle et al. (*Cell* 75, 135–46 (1993)). A human CIITA cDNA (Riley et al., *Immunity* 2, 533–43 (1995)) (generously provided by Dr. Jeremy M. Boss) was used as a template for the PCR.

Twelve overlapping CIITA genomic clones were isolated, plaque purified, and mapped by Southern blot analyses (FIG. 1). DNA prepared from each clone by precipitation with polyethylene glycol (Malik et al., *Nuc. Acids Res.* 18, 4031–32 (1990)) was digested with Not I to excise the genomic insert from the vector DNA and subsequently digested with Hind III. All restriction enzymes were from New England Biolaboratories, Beverly, Mass. After electrophoresis in 1% agarose, the DNA was depurinated in 2.5 M HCl, denatured in 1.5 M NaCl, 0.5 M NaOH, and transferred to Nytran (Schleicher & Schuell, Keene, N.H.) by capillary blotting. Filters were baked at 90° C. for 1 hr, and probed as described above. Duplicate filters were prehybridized for 1 hr at 42° C. in 6×SSC, 5×Denhart's solution, 1% SDS, and 100 μg/ml boiled salmon sperm DNA; then hybridized at 42° C. for 18 hr in the same solution with 3×10$^{-12}$ mol of [$^{32}$P]-end-labeled 5' UTR oligonucleotide added. The 5' UTR oligonucleotide: 5' AGGATGCCTTCGGATGC-CCAGCTCAGAAGC 3' (SEQ ID NO:4), which corresponds to the reverse complement of nt 15 to 44 of the human CIITA cDNA sequence described above (also see FIG. 2C), was 5'-end-labeled using T4 polynucleotide kinase (New England Biolaboratories) and γ-[$^{32}$P]-ATP (3000 Ci/mmol; Dupont NEN Research Products). J. SAMBROOK ET AL., MOLECULAR CLONING: A LABORA- TORY MANUAL (2d ed. 1989). These duplicate filters were washed in 6×SSPE, 0.1% SDS at 42° C. and visualized by autoradiography using an intensifying screen and Kodak XAR-5 film.

Two overlapping clones (CIITA10 and CIITA12) that hybridize to the 5' UTR oligonucleotide were subjected to additional Southern blot analyses allowing localization of this probe to the 3' end of an approximately 6.7 kb Xba I genomic DNA fragment (FIGS. 2A and 2B). This fragment was subcloned into pBluescript II (Stratagene), and an approximately 1 kb fragment from the 3' end of the Xba I fragment was liberated by cutting with Kpn I (FIG. 2B—nucleotides 5720 to 6678 of SEQ ID NO:1). This fragment was sequenced by the dideoxy chain-termination method (Sanger et al., *Proc. Nat'l Acad. Sci. USA* 74, 5463–67 (1977)), using Sequenase (United States Biochemical Corp., Cleveland, Ohio) (FIG. 2C). The 3' end of exon 1 of human CIITA was determined by a comparison of the genomic DNA sequence to the sequence of the human CIITA cDNA (Steimle et al., *Cell* 75, 135–46 (1993)), and the 5' end of exon 1 was determined by mapping the transcriptional start site as described below.

EXAMPLE 3
Identification of CIITA Transcriptional Start Site by Primer Extension Primer extension analysis of the CIITA mRNA was performed using Raji poly A+RNA as previously described (Wright et al., *J. Exp. Med.* 181, 1459–71 (1995)) using the 5' UTR oligonucleotide described above. Absolute product lengths were obtained by comparison to a sequencing ladder. One predominant transcriptional start site for the human CIITA gene was identified (FIG. 2C). This start site is located very close (within 4 bp) to the end of the human CIITA cDNA reported by Steimle et al. (*Cell* 75, 135–46 (1993)).

EXAMPLE 4
Sequencing of the 6.7 kilobase Xba I Genomic DNA Fragment

The original 6.7 kb Xba I genomic DNA fragment isolated from clone 10 (FIG. 2B) was subcloned into pBluescript II (SK-) (Stratagene, La Jolla, Calif.). The sequence of the 3' Kpn I-Xba I fragment (nucleotides 5720 to 6678 of SEQ ID NO:1) (shown in FIG. 2C) was obtained by manual sequencing of this cloned DNA in pBluescript II using the dideoxy chain-termination method (Sanger et al., *Proc. Nat'l Acad. Sci USA* 74, 5463–67 (1977)), using Sequenase (United States Biochemical Corp., Cleveland, Ohio). The rest of the 6.7 kb Xba I genomic DNA fragment (nucleotides 1 to 5720 of SEQ ID NO:1) was sequenced by the University of North Carolina-Chapel Hill Automated DNA Sequencing Facility on a Model 373A DNA Sequencer (Applied Biosystems, Foster City, Calif.) using the Taq DYEDOXY™ Terminator Cycle Sequencing Kit (Applied Biosystems). Sanger et al., *BioTechniques* 7, 5463–67 (1977); Carothers et al., *Proc. Nat'l Acad. Sci. USA* 74, 494–99 (1989). The M13 forward and M13 reverse sequencing primers were used initially. Additional internal primers were synthesized and used to obtain the complete sequence of the fragment. A large portion of the sequence was rechecked by sequencing the opposite strand. As a result, most of the length of the fragment has been sequenced on both strands.

EXAMPLE 5
Constructs

The positive control plasmid pDR.Luc was constructed by cloning the -267 to +27 region of the proximal promoter of the class II MHC gene HLA-DRα into pGL2-Basic as a Hind III-Kpn I fragment.

Figure 3:
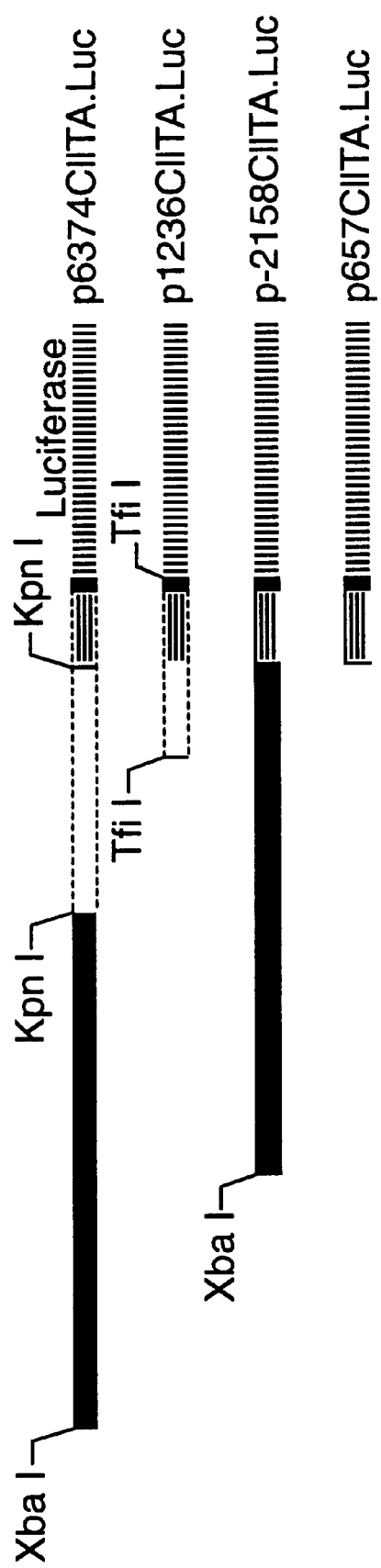
FIG. 3. Schematic diagram of the CIITA regulatory element constructs. A Tfi I DNA fragment (nucleotides 5122 to 6374 of SEQ ID NO:1—see FIG. 2B) containing 112 bp of 5' UTR (shown as a small black box) and 1124 bp of 5' flanking sequences of the human CIITA gene were cloned upstream of the luciferase reporter gene (vertical lined box) in the pGL2-Basic vector (Promega) to create the plasmid p1236CIITA.Luc. This Tfi I fragment was digested with Kpn I to create a smaller fragment (small black and horizontal lined boxes—nucleotides 5717 to 6374 of SEQ ID NO: 1) containing the 112 bp of 5' UTR and 546 bp of flanking sequence in p657CIITA.Luc. An approximately 3.6 kb Xba I-Kpn I fragment (large black box—nucleotides 1 to 3557 of SEQ ID NO:1) was added to p657CIITA.Luc to create p-2158CIITA.Luc, which lacks a central 2158 bp Kpn I fragment (white box—nucleotides 3562 to 5720 of SEQ ID NO:1) found in the original 6678 bp Xba I fragment. This central fragment was added to p-2158CIITA.Luc reconstituting in the plasmid p6374CIITA.Luc the approximately 6.4 kb of native CIITA 5' flanking sequences (including the 5' end of the CIITA gene), excluding the 304 bp Tfi I-Xba I fragment (nucleotides 6374 to 6678 of SEQ ID NO:1) found at the 3' end of clone 10 (see FIG. 2B).

Tfi I digestion was used to liberate a fragment (nucleotides 5122 to 6370 of SEQ ID NO:1), containing 112 bp of 5' UTR and 1124 bp of 5' flanking sequences of the human CIITA gene (FIGS. 2B and 2C). This Tfi I fragment was blunted and cloned into the Sma I site upstream of the luciferase reporter gene in the pGL2-Basic vector (Promega, Madison, Wis.) to create the plasmid, pl236CIITA.Luc (FIG. 3). The Tfi I fragment was digested with Kpn I to create a smaller fragment (nucleotides 5717 to 6374 of SEQ ID NO:1) containing 112 bp of 5' UTR and 546 bp of flanking sequence, which was cloned into the Kpn I site in the polylinker of pGL2-Basic vector to create p657CIITA.Luc. A two-step cloning procedure was then employed to construct a plasmid containing all of the flanking sequences present in the original approximately 6.7 kb Xba I fragment of clone 10 (FIG. 2B). In the first step, the approximately 3.6 kb Xba I-Kpn I fragment (nucleotides 1 to 3557 of SEQ ID NO:1) was cloned into the Kpn I site (nucleotide 5720 of SEQ ID NO:1) of p657CIITA.Luc to form the plasmid, p-2158CIITA.Luc. In the second step, the central 2158 bp Kpn I fragment (nucleotides 3562 to 5720 of SEQ ID NO:1) was added to p-2158CIITA.Luc reconstituting in plasmid, p6374CIITA.Luc, the native 6374 bp of CIITA 5' flanking sequences (including the 5' end of the CIITA gene) found in the original Xba I fragment, excluding the 304 bp Tfi I-Xba I fragment (nucleotides 6374 to 6678 of SEQ ID NO:1) at the 3' end of clone 10. A second deletion construct, p-3538CIITA.Luc was generated by blunt cloning a 2182 bp Xba I-Sph I fragment (nucleotides 1 to 2182 of SEQ ID NO:1) into the Kpn I site (nucleotide 5720 of SEQ ID NO:1) of p657CIITA.Luc.

As both plasmid p-2158CIITA.Luc and p6374CIITA.Luc are inducible by IFN-γ, we conclude that this activity is localized to the approximately 3.6 kb Xba I-Kpn I fragment (nucleotides 1 to 3557 of SEQ ID NO:1). Further studies with p-3538CIITA.Luc suggest that the IFN-γ inducibility may be further localized to the approximately 2.2 kb Xba I-Sph I fragment (nucleotides 1 to 2182 of SEQ ID NO:1).

EXAMPLE 6
Transfections and Luciferase Assay

Ten micrograms of plasmid DNA were used in each transfection. Transient transfections were performed by electroporation using a Bio-Rad gene pulser. 3×10⁶ cells in 300 µl of medium were pulsed at 200 mV at a capacitance setting of 960 µF. After transfection cell were placed into 10 ml of complete medium. Raji cells were harvested for luciferase assays 48 hours after transfection. Transfected human glioma cells were allowed to adhere for 6 hours after transfection and then treated with 500 U/ml of recombinant human IFN-γ (Genentech, South San Francisco, Calif.) for 16 hours before harvesting of the cells for luciferase assays. Luciferase assays were performed using an LB 953 AutoLumat (EG&G Berthold) as previously described. Brasier et al., *BioTechniques* 7, 1116–22 (1989).

Transient transfection of RAW 264.7 cells for TGF-β studies was performed by DEAE-dextran by a protocol used by Nicolet & Paulnock. *J. Immunol.* 152, 153–62 (1994). Briefly, 5×10⁶ cells were plated into 60 mm dishes and allowed to grow overnight. Medium was removed and dishes were rinsed with TBS-D (Tris-buffered saline containing 0.1% dextrose). Dishes received one ml of a mixture containing DNA (2.5 µg per 60 mm dish) and 300 µg of DEAE-dextran in TBS-D, and were incubated for 3 hr. TBS-D/DNA/DEAE-dextran was removed and replaced with 1 ml of PBS containing 10% DMSO for 1 minute.

Dishes were washed with PBS and incubated overnight in culture medium before treatments. Cells were pretreated with murine TGF-β1 (R&D Systems, Minneapolis, Minn.) as indicated before treatment with murine IFN (200 U/ml) (Genzyme, Cambridge, Mass.) for 12 hr and harvesting for luciferase assays.

Transient transfection of U3A cells for STAT1 studies was performed by the calcium phosphate co-precipitation method. SAMBROOK ET AL., MOLECULAR CLONING: A LABORATORY MANUAL (2d ed. 1989). Cells were plated in 10 cm dishes at a density of $5\times10^5$ cells and transfected 24 h later. Ten µg of reporter construct, or 10 µg of reporter construct in combination with 10 µg of either pCDNA3 (Invitrogen Corp., Carlsbad, Calif.) or the STAT1 expression vector were added to each dish of cells, and dishes were incubated at 37° C. in 5% $CO_2$. After 6 hr, the precipitates were removed, and dishes were rinsed twice with 1×PBS. Culture medium (10 ml) was added with or without 500 U/ml of recombinant human IFN-γ (Genentech). Cells were harvested for luciferase assays 14–16 h later. The STAT1 expression vector (generously provided by Dr. James Darnell, Jr., Rockefeller University, New York, N.Y.) has been previously described. Improta et al., *Proc. Nat'l Acad. Sci. USA* 91, 4776–80 (1994). The empty pCDNA3 vector was used as a negative control. The pDR.Luc reporter construct was used as a positive control.

EXAMPLE 7
Activity of the CIITA Regulator Element in a Human B Cell Line

Figure 4:
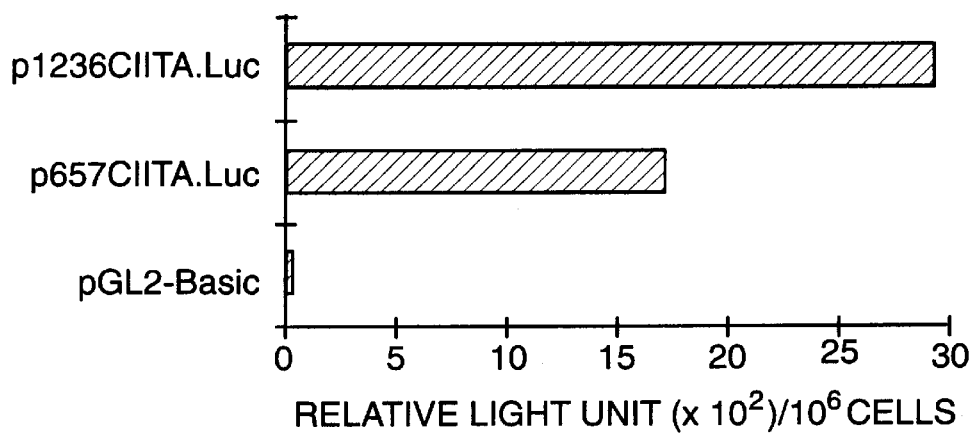
FIG. 4. Activity of the CIITA regulatory element in a human B cell line. Transient transfections of Raji cells using 10 µg of plasmid DNA were performed by electroporation. Cells were harvested for luciferase assays 48 hours after transfection. Luciferase activity was measured as relative light units×10² per million cells. The pGL2Basic vector (Promega) is a promoterless vector that was used as a negative control.

Raji cells, which exhibit constitutive expression of the CIITA gene, were transiently transfected with the human genomic CITA constructs as described in Example 6. Forty-eight hours after transfection, cells were harvested for luciferase assays. Luciferase activity was measured as relative light units (RLU)×$10^2$ per million cells. (FIG. 4). The pGL2-Basic vector (Promega) is a promoterless vector that was used as a negative control. Transfection of either p657CIITA.Luc or p1236CIITA.Luc resulted in high levels of luciferase expression as compared with transfection with pGL2-Basic. It appears that the p657CIITA. Luc and p1236CIITA.Luc constructs contain regulatory sequences driving constitutive expression of the CIITA gene in Raji cells.

Figure 5:
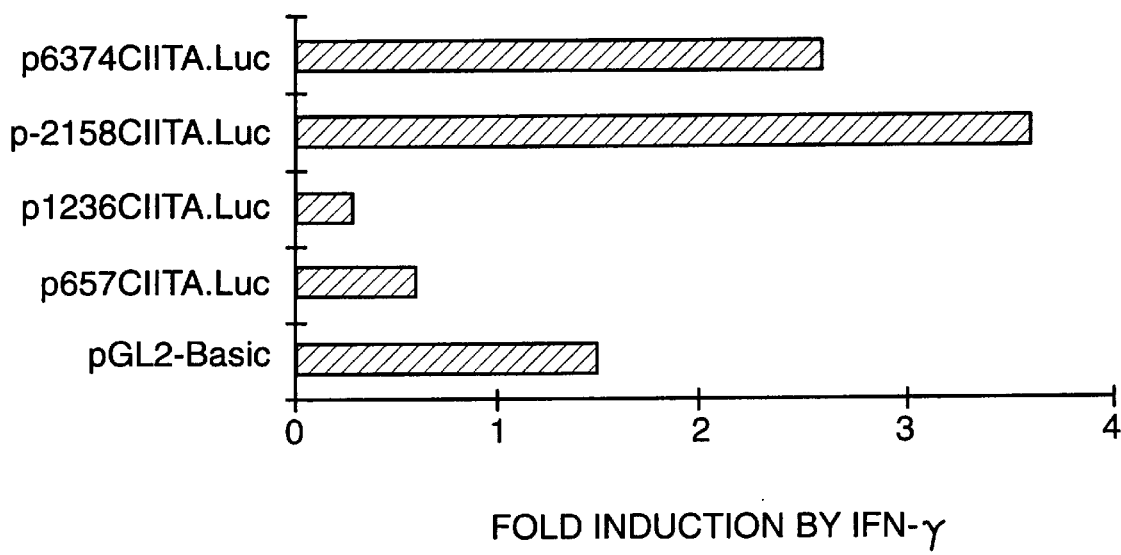
FIG. 5. Activity of the CIITA regulatory element in an IFN-γ responsive glioblastoma cell line. U373 MG cells were transiently transfected by electroporation using 10 µg of plasmid DNA and were allowed to adhere for 6 hours after transfection, and then treated with 500 U/ml of recombinant human IFN-γ for 16 hours before harvesting. Luciferase activity was measured as relative light units (RLU) per µg of protein. Fold induction after IFN-γ treatment was calculated by dividing the RLU of IFN-γ treated samples by the RLU of untreated samples.

EXAMPLE 8
Activity of the CIITA Regulatory Element in an IFN-γ Responsive Glioblastoma Cell Line U373 MG cells, which express MHC class II antigens in response to IFN-γ, were transiently transfected with the human genomic CIITA constructs as described in Example 6. Transfected cells were treated with 500 U/ml of recombinant human IFN-γ for 16 hours prior to harvesting for luciferase assays. Fold induction in luciferase activity after IFN-γ treatment (calculated by dividing the RLU of IFN-γ-treated samples by the RLU of untreated samples) is shown in FIG. 5. The luciferase expression of p657CIITA.Luc and p1236CIITA.Luc was below that of the promoterless pGL2-Basic vector. An IFN-γ response was detected with both plasmids p6374CIITA.Luc and p-2158CIITA.Luc, indicating that IFN-γ responsive elements are not present in the central 2158 bp Kpn I fragment (FIG. 3, white box) (nucleotides 3562 to 5720 of SEQ ID NO:1).

EXAMPLE 9
Induction of p-2158CIITA.Luc and p-3538CIITA.Luc by IFN-γ

To further localize the IFN-γ responsive element within the 5' flanking sequences of the CIITA gene, U373 MG cells were transiently transfected with the p-2158CIITA and p-3538CIITA.Luc constructs and the fold induction in luciferase activity by IFN-γ was measured as described in Examples 6 and 8. The data are presented below in Table 1. These results confirm that the IFN-γ responsive element is likely associated with the approximately 3.6 kb Xba I-Kpn I fragment in p-2158CIITA.Luc (nucleotides 1 to 3562 of SEQ ID NO:1). Furthermore, these data suggest that the IFN-γ responsive element can be further localized to the approximately 2.2 kb Xba I-Sph I fragment present in both p-3538CIITA.Luc and p-2158CIITA.Luc (nucleotides 1 to 2182 in SEQ ID NO:1), and is not associated with the central 3538 bp Sph I-Kpn I fragment (nucleotides 2182 to 5720 in SEQ ID NO:1).

TABLE 1

| Induction of Luciferase Activity by IFN-γ | |
|---|---|
| Construct | Fold Induction |
| pGL2-Basic | 0.8 |
| p-2158CIITA.Luc | 1.5 |
| p-3538CIITA.Luc | 1.7 |

EXAMPLE 10
TGF-β1 Suppresses Inducibility of the 5' Flanking Region of the CIITA Gene in Response to IFN-γ

TGF-β has been shown to inhibit the IFN-γ-induced transcription of class II MHC genes in a number of different cell types. Panek et al., *J. Immunol.* 154, 2846–54 (1995); Devajyothi et al., *J. Biol. Chem.* 268, 18794–18800 (1993); Reimold et al., *J. Immunol.* 151, 4173–82 (1993). Recent data indicate that pretreatment of macrophage cell lines with TGF-β1 causes a reduction in the increased levels of steady-state CIITA mRNA that occur in response to IFN-γ. Nandan & Reiner, *J. Immunol.* 158, 1095–1101 (1997); Lee et al., *J. Immunol.* 158, 2065–75 (1997). The mechanism of this inhibition may involve suppression of the induction of the CIITA regulatory elements disclosed herein by IFN-γ.

Figure 6:
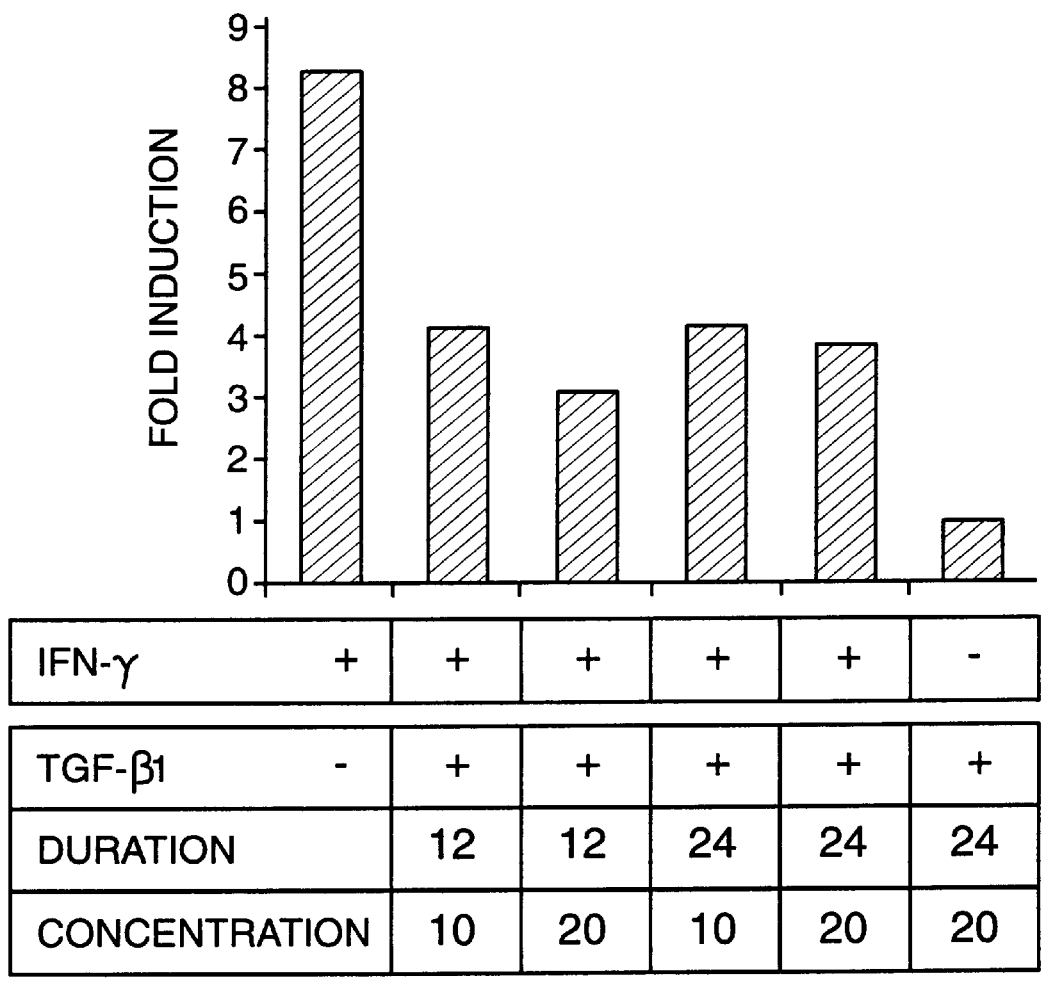
FIG. 6. TGF-β1 suppresses IFN-γ-induction of the regulatory sequences of the CIITA gene in RAW 264.7 cells. RAW 264.7 cells were transiently transfected with the p-2158CIITA.Luc plasmid using DEAE-dextran. Cells were plated at a density of $5 \times 10^6$ cells/60 mm dishes and allowed to grow overnight. Medium was removed and dishes were rinsed with TBS-D. Dishes received one ml of a mixture containing DNA (2.5 µg per 60 mm dish) and 300 µg of DEAE-dextran in TBS-D, and were incubated for 3 hr. TBS-D/DNA/DEAE-dextran was removed and replaced with 1 ml of PBS containing 10% DMSO for 1 minute. Dishes were washed with PBS and incubated overnight in culture medium before treatments. Cells were pretreated with murine TGF-β1 as indicated before treatment with murine IFN-γ (200 U/ml) for 12 hr and harvesting for luciferase assays. Duration of TGF-β1 pretreatment was 12 hr or 24 hr, concentration of TGF-β1 was 10 or 20 ng/ml. Luciferase activity was measured as RLU per µg of protein. Fold induction after IFN-γ treatment was calculated by dividing the RLU of IFN-γ-treated samples by the RLU of untreated samples. This experiment is representative of three independent experiments.

To investigate this possibility, RAW 264.7 cells were transiently transfected with the p-2158CIITA.Luc plasmid, and luciferase activity was measured as described in Examples 6 and 8. The luciferase activity of p-2158CIITA.Luc is activated approximately 8-fold after 12 hr of IFN-γ treatment in these cells (FIG. 6). Pretreatment of the cells for 12 hr or 24 hr with either 10 ng/ml or 20 ng/ml TGF-β1 results in a reduction in this IFN-γ-induced luciferase activity of approximately 50%. TGF-β1 treatment alone does not significantly alter the basal luciferase activity of the p-2158CIITA.Luc plasmid in these cells. In three independent experiments, the induction of p-2158CIITA.Luc by IFN-γ ranged from 4–8 fold and suppression by TGF-β1 ranged from 37–63% with an average suppression of 44% for 10 treatment groups.

EXAMPLE 11
STAT1 Activates the Inducibility of the 5' Flanking Region of the CIITA Gene in Response to IFN-γ

To investigate the role of STAT1 in activation of IFN-γ inducibility of the 5' flanking sequences of the CIITA gene, STAT1 defective U3A cells were transiently transfected with the p6374CIITA.Luc in combination with a STAT1 expression vector plasmid (Improta et al., *Proc. Nat'l Acad. Sci. USA* 91, 4776–80 (1994)), and luciferase activity was measured as described in Examples 6 and 8. The empty expression vector, pCNDA3, was included as a negative control. The pDR.Luc reporter construct was used as a positive control. The pDR.Luc plasmid contains the S, X1, X2 and Y regulatory elements of the class II MHC gene HLA-DRα, which have been shown to be required for activation of this promoter by CIITA in response to IFN-γ. Zhou & Glimcher, *Immunity* 2, 545–53 (1995); Riley et al., *Immunity* 2, 533–43 (1995).

Figure 7:
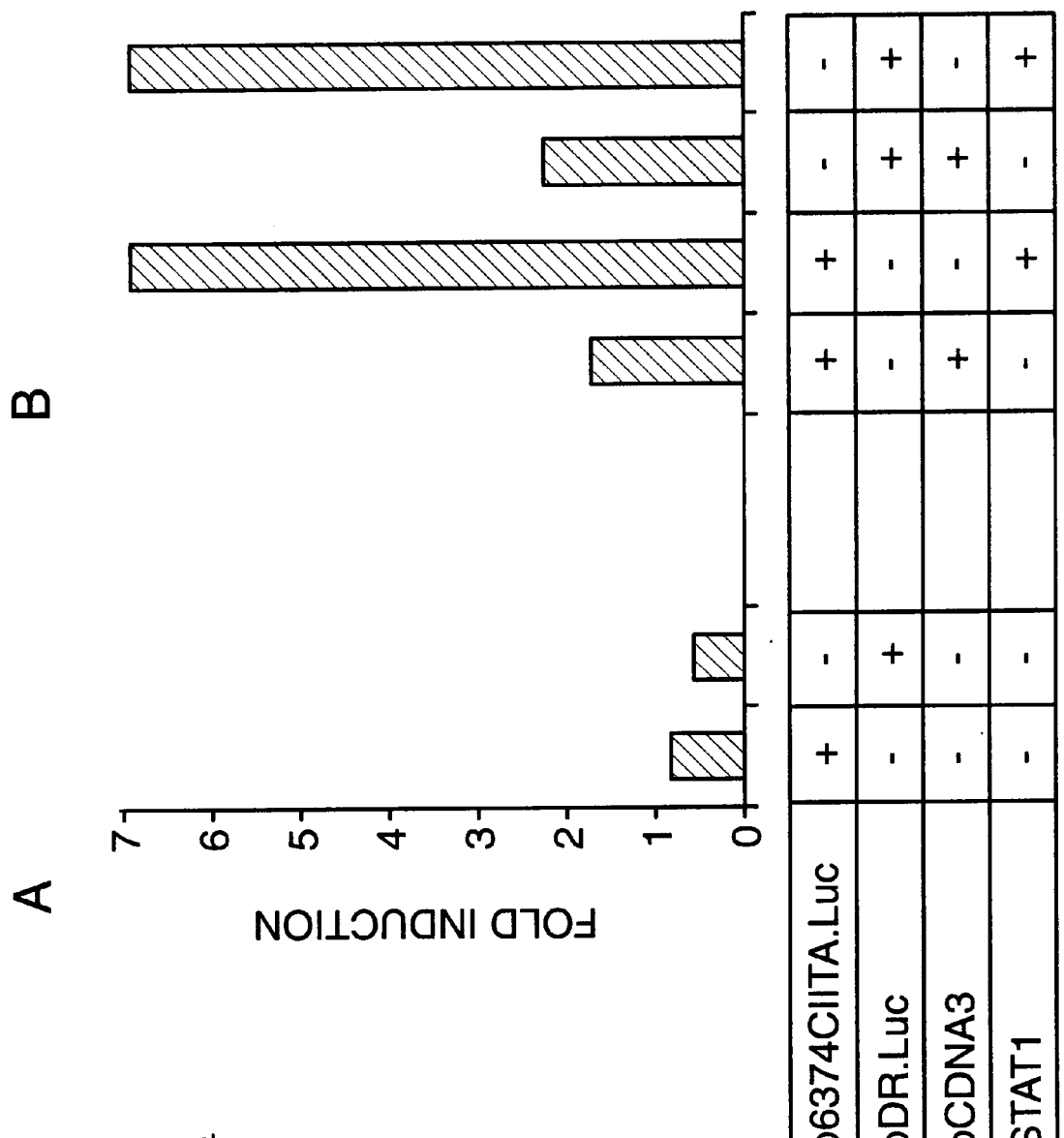
FIGS. 7A–B. STAT1 regulates induction of the 5' flanking region of the human CIITA gene by IFN-γ. The data presented in panels A and B are from different experiments.

As demonstrated in FIG. 7A, neither the luciferase activity of p6374CIITA.Luc nor pDR.Luc is activated by IFN-γ treatment alone in U3A cells. FIG. 7B presents a representative experiment of three independent experiments showing the stimulatory effect of over-expression of STAT1 on IFN-γ induction of p6374CIITA. Luc. STAT1 reproducibly activated the IFN-γ induced luciferase activity of the p6374CIITA.Luc plasmid from 2 to 4 fold as compared with the stimulatory activity of the pCDNA3 control vector alone. As IFN-γ is required for activation of the STAT1 protein by phosphorylation, co-transfection of U3A cells with p6374CIITA.Luc or pDR.Luc and the STAT1 expression vector did not stimulate luciferase activity in the absence of IFN-γ treatment (data not shown).

The foregoing Examples are illustrative of the present invention, and are not to be construed as limiting thereof. The invention is defined by the following claims, with equivalents of the claims to be included therein.

That which is claimed:

1. An isolated DNA comprising a Class II Transactivator regulatory element selected from the group consisting of:
   (a) DNA consisting of SEQ ID NO:1; and
   (b) DNA that hybridizes to DNA of SEQ ID NO:1 under stringent conditions, defined by a wash stringency of 0.3 M NaCl. 0.03 M sodium citrate, 0.1% SDS at 60° C., and encodes a Class II Transactivator regulatory element.

2. An isolated DNA comprising a Class II Transactivator regulatory element selected from the group consisting of (a) DNA consisting of nucleotides 1 to 3562 of SEQ ID NO:1; and (b) DNA that hybridizes to DNA of nucleotides 1 to 3562 of SEQ ID NO:1 under stringent conditions, defined by a wash stringency of 0.3 M NaCl, 0.03 M sodium citrate, 0.1% SDS at 60° C., and encodes a Class II Transactivator regulatory element.

3. An isolated DNA comprising a Class II Transactivator regulatory element selected from the group consisting of (a) DNA consisting of nucleotides 1 to 2182 of SEQ ID NO:1; and (b) DNA that hybridizes to DNA of nucleotides 1 to 2182 of SEQ ID NO:1 under stringent conditions, defined by a wash stringency of 0.3 M NaCl, 0.03 M sodium citrate, 0.1% SDS at 60° C., and encodes a Class II Transactivator regulatory element.

4. The isolated DNA of claim 1, wherein said regulatory element activates transcription of the Class II transactivator gene.

5. The isolated DNA of claim 1, wherein said regulatory element suppresses transcription of the Class II transactivator gene.

6. The isolated DNA of claim 1, wherein said regulatory element is an interferon-γ responsive regulatory element.

7. The isolated DNA of claim 1, wherein said regulatory element is a transforming growth factor-β responsive regulatory element.

8. A recombinant DNA comprising the isolated DNA of claim 1 operably associated with a heterologous DNA.

9. The recombinant DNA according to claim 8, wherein said heterologous DNA encodes a reporter protein.

10. A cell containing a recombinant DNA according to claim 8.

11. The cell according to claim 10, wherein said cell is a mammalian cell.

12. The cell according to claim 10, wherein said cell is a human cell.

13. The cell according to claim 10, wherein said cell is selected from the group consisting of B lymphocytes, T lymphocytes, Kupffer cells, lymphoma cells, dendritic cells, astrocytes, intestinal and colonic epithelial cells, macrophages, monocytes, glioblastoma cells, endothelial cells, Langerhans cells, fibroblasts, and microglia cells.

14. The cell according to claim 10, wherein said cell exhibits inducible expression of the Class II Transactivator gene.

15. The isolated DNA of claim 1, wherein said regulatory element comprises a STAT1 response element.

16. An isolated DNA comprising a Class II Transactivator regulatory element selected from the group consisting of (a) DNA consisting of nucleotides 1 to 6374 of SEQ ID NO:1; and (b) DNA that hybridizes to DNA of nucleotides 1 to 6374 of SEQ ID NO:1 under stringent conditions, defined by a wash stringency of 0.3 M NaCl, 0.03 M sodium citrate, 0.1% SDS at 60° C., and encodes a Class II Transactivator regulatory element.

17. An isolated DNA comprising a Class II Transactivator regulatory element selected from the group consisting of (a) DNA consisting of nucleotides 5717 to 6374 of SEQ ID NO:1; and (b) DNA that hybridizes to DNA of nucleotides 5717 to 6374 of SEQ ID NO:1 under stringent conditions, defined by a wash stringency of 0.3 M NaCl, 0.03 M sodium citrate, 0.1% SDS at 60° C., and encodes a Class II Transactivator regulatory element.

18. The isolated DNA of claim 1 consisting of SEQ ID NO:1.

19. The isolated DNA of claim 2 consisting of nucleotides 1 to 3562 of SEQ ID NO:1.

20. The isolated DNA of claim 2, wherein said regulatory element activates transcription of the Class II transactivator gene.

21. The isolated DNA of claim 2, wherein said regulatory element suppresses transcription of the Class II transactivator gene.

22. The isolated DNA of claim 2, wherein said regulatory element is an interferon-γ responsive regulatory element.

23. The isolated DNA of claim 2, wherein said regulatory element is a transforming growth factor-β responsive regulatory element.

24. A recombinant DNA comprising the isolated DNA of claim 2 operably associated with a heterologous DNA.

25. The isolated DNA of claim 2, wherein said regulatory element comprises a STAT1 response element.

26. A cell containing a recombinant DNA according to claim 24.

27. The isolated DNA of claim 3 consisting of nucleotides 1 to 2182 of SEQ ID NO:1.

28. The isolated DNA of claim 3, wherein said regulatory element activates transcription of the Class II transactivator gene.

29. The isolated DNA of claim 3, wherein said regulatory element suppresses transcription of the Class II transactivator gene.

30. The isolated DNA of claim 3, wherein said regulatory element is an interferon-γ responsive regulatory element.

31. The isolated DNA of claim 3, wherein said regulatory element is a transforming growth factor-β responsive regulatory element.

32. A recombinant DNA comprising the isolated DNA of claim 3 operably associated with a heterologous DNA.

33. A cell containing a recombinant DNA according to claim 32.

34. The isolated DNA of claim 3, wherein said regulatory element comprises a STAT1 response element.

35. The isolated DNA according to claim 16 consisting of nucleotides 1 to 6374 of SEQ ID NO:1.

36. A recombinant DNA comprising the isolated DNA of claim 16 operably associated with a heterologous DNA.

37. A cell containing a recombinant DNA according to claim 36.

38. The isolated DNA according to claim 17 consisting of nucleotides 5717 to 6374 of SEQ ID NO:1.

39. A recombinant DNA comprising the isolated DNA of claim 17 operably associated with a heterologous DNA.

40. A cell containing a recombinant DNA according to claim 39.

* * * * *